US008757077B2

(12) United States Patent
Edelson et al.

(10) Patent No.: US 8,757,077 B2
(45) Date of Patent: Jun. 24, 2014

(54) SPAR MOORING LINE SHARING METHOD AND SYSTEM

(75) Inventors: David N. Edelson, Houston, TX (US); Jim Wang, Houston, TX (US); Andrew Buck, Perth (AU); Peter Sharp, Paris (FR); Timothy Arthur Hale, Claremont (AU)

(73) Assignee: Technip France, Courbevoie (FR)

( * ) Notice: Subject to any disclaimer, the term of this patent is extended or adjusted under 35 U.S.C. 154(b) by 290 days.

(21) Appl. No.: 13/266,481

(22) PCT Filed: Apr. 30, 2010

(86) PCT No.: PCT/US2010/033126
§ 371 (c)(1),
(2), (4) Date: Apr. 26, 2012

(87) PCT Pub. No.: WO2010/127220
PCT Pub. Date: Nov. 4, 2010

(65) Prior Publication Data
US 2012/0266800 A1    Oct. 25, 2012

Related U.S. Application Data

(60) Provisional application No. 61/174,425, filed on Apr. 30, 2009.

(51) Int. Cl.
*B63B 21/00*    (2006.01)
*B63B 21/50*    (2006.01)

(52) U.S. Cl.
CPC ..................................... *B63B 21/50* (2013.01)
USPC ...................................................... 114/230.2

(58) Field of Classification Search
USPC ............... 114/200, 230, 230.2; 405/223.1
See application file for complete search history.

(56) References Cited

U.S. PATENT DOCUMENTS

| 4,351,258 A * | 9/1982 | Ray et al. ................. 114/230.24 |
| 5,095,841 A * | 3/1992 | Santos et al. ...................... 441/3 |
| 5,507,598 A * | 4/1996 | Huete ........................ 405/223.1 |
| 2008/0282955 A1 * | 11/2008 | Horton et al. ................. 114/200 |

FOREIGN PATENT DOCUMENTS

EP           0 831 023        3/1998

OTHER PUBLICATIONS

Raffaelli, L., International Search Report for International Patent Application No. PCT/US2010/033126, European Patent Office, dated Oct. 21, 2010.
Raffaelli, L., Written Opinion for International Patent Application No. PCT/US2010/033126, European Patent Office, dated Oct. 21, 2010.

* cited by examiner

*Primary Examiner* — Lars A Olson
*Assistant Examiner* — Jovon Hayes
(74) *Attorney, Agent, or Firm* — Locke Lord LLP

(57) ABSTRACT

The disclosure provides a method and system of coupling end-to-end at least two existing mooring lines (12A, 12B) that are already deployed from the floating platform (56) to the seabed or other connecting structure to create a single shared line from the two lines. The shared lines then form a single looped line with both ends deployed to the subsea connections. The shared length provides enough payout of line to loosen one line sufficiently, while the other line becomes correspondingly tighter using the catenary length of the tight line. In part, the line can be loosened while the other is tightened because the lines are generally in the same overall direction to the seabed, such as in a same quadrant around the platform. Thus, the lines share their available lengths to provide the necessary payout for the repairs.

17 Claims, 16 Drawing Sheets

SPAR MOORING LINE SHARING METHOD AND SYSTEM

CROSS REFERENCE TO RELATED APPLICATIONS

This application claims the benefit of U.S. Provisional Application No. 61/174,425, filed Apr. 30, 2009, titled "Spar Mooring Line Sharing Method and System."

STATEMENT REGARDING FEDERALLY SPONSORED RESEARCH OR DEVELOPMENT

Not applicable.

REFERENCE TO APPENDIX

Not applicable.

BACKGROUND OF THE INVENTION

1. Field of the Invention

This disclosure relates to a method and system of securing floating platforms and other vessels. More specifically, the disclosure relates to a method and system for securing the floating platforms and other vessels with shared mooring lines.

2. Description of the Related Art

Deep-water offshore platforms, including Spars, are generally moored to the seabed through catenary mooring lines, such as chains and cables. These mooring lines are connected between the platforms on one end and structures on the seabed on the other end. The lengths can be significant and in many cases exceed one or more kilometers (or miles).

Movement of the offshore platform relative to the seabed is generally accommodated and factored into the weight, strength, length of the lines and seabed structures, and other parameters, so that under normal conditions, the system remains connected between the platform and seabed. However, there are sometimes unforeseen events that can cause an overload condition. It is known that an overload condition can break or otherwise destroy at least a portion of the connections, including the lines and anchors holding the lines to the seabed, at considerable expense.

When repairs are required to a connection, it is sometimes necessary to loosen the tension on the line to be able to cut or generally disassemble the connection, so that the repairs can be accomplished. However, due to the significant length and size of a typical mooring line, there is generally insufficient payout of line available to be able to adequately loosen the line.

One option is to specially attach additional line to the end of the existing mooring line to be able to payout the line farther. While in the abstract, such a remedy would seem natural, the size and length of the lines does not make this option particularly suitable. For example, a typical 60 feet of chain weighs about 2,500 kilograms and about 00 feet can be needed for one line for sufficient payout of line. Loading 12,500 kilograms of large size chain for each mooring line needing repair down into the depths of a floating platform that is in production with explosive hydrocarbons is risky at best.

Another option is to move the floating platform closer to the seabed connection to provide more payout of the line. However, movement in one direction presupposes that there is enough payout in the opposite direction, which is generally insufficient as discussed above. Further, the floating platform is generally connected to multiple production risers. A large movement of the platform can disrupt the connections and is generally not a satisfactory solution.

Therefore, there remains a need for a method and system for providing an increased payout of a mooring line without necessitating supplying additional quantities of lines to the existing lines on the floating platform.

SUMMARY OF THE INVENTION

The disclosure provides a method and system of coupling end-to-end at least two existing mooring lines that are already deployed from the floating platform to the seabed or other connecting structure to create a single shared line from the two lines. Each line is locked into position and disconnected from the platform structure, so that an end of each line is relatively free to be coupled to the other line through a coupling member. The shared lines then form a single looped line with both ends deployed to the subsea connections. The shared length (such as double the length of a single line if both lines were deployed the same distance) provides enough payout of line to loosen one line sufficiently, while the other line becomes correspondingly tighter using the catenary length of the tight line. In part, the line can be loosened while the other is tightened because the lines are generally in the same overall direction to the seabed, such as in a same quadrant around the platform. Thus, the lines share their available lengths to provide the necessary payout for the repairs.

The disclosure provides a method for sharing of mooring lines, comprising: coupling end-to-end at least a first mooring line and a second mooring line that are already deployed from a floating platform to a seabed or other connecting structure to create a single shared line from the two lines with the ends of the shared line deployed to the seabed or other connecting structure; tightening the first mooring line to provide payout of line for the second mooring line; and loosening the second mooring line.

The disclosure provides a system for sharing of mooring lines, comprising: at least one holding element adapted to hold at least a first mooring line and a second mooring line with ends available for coupling, the mooring lines being already deployed from a floating platform to couple with a seabed or other connecting structure with other ends of the lines; a coupling element adapted to couple end-to-end the two mooring lines to create a single shared line from the two lines; and a first tightening element adapted to tighten the first mooring line to provide payout of line for the second mooring line to allow loosening of the second mooring line.

BRIEF DESCRIPTION OF THE SEVERAL VIEWS OF THE DRAWINGS

FIG. 17 is a schematic top view of one platform chain being paid out while the other platform chain of the pair is hauled in.

DETAILED DESCRIPTION

Figure 1:
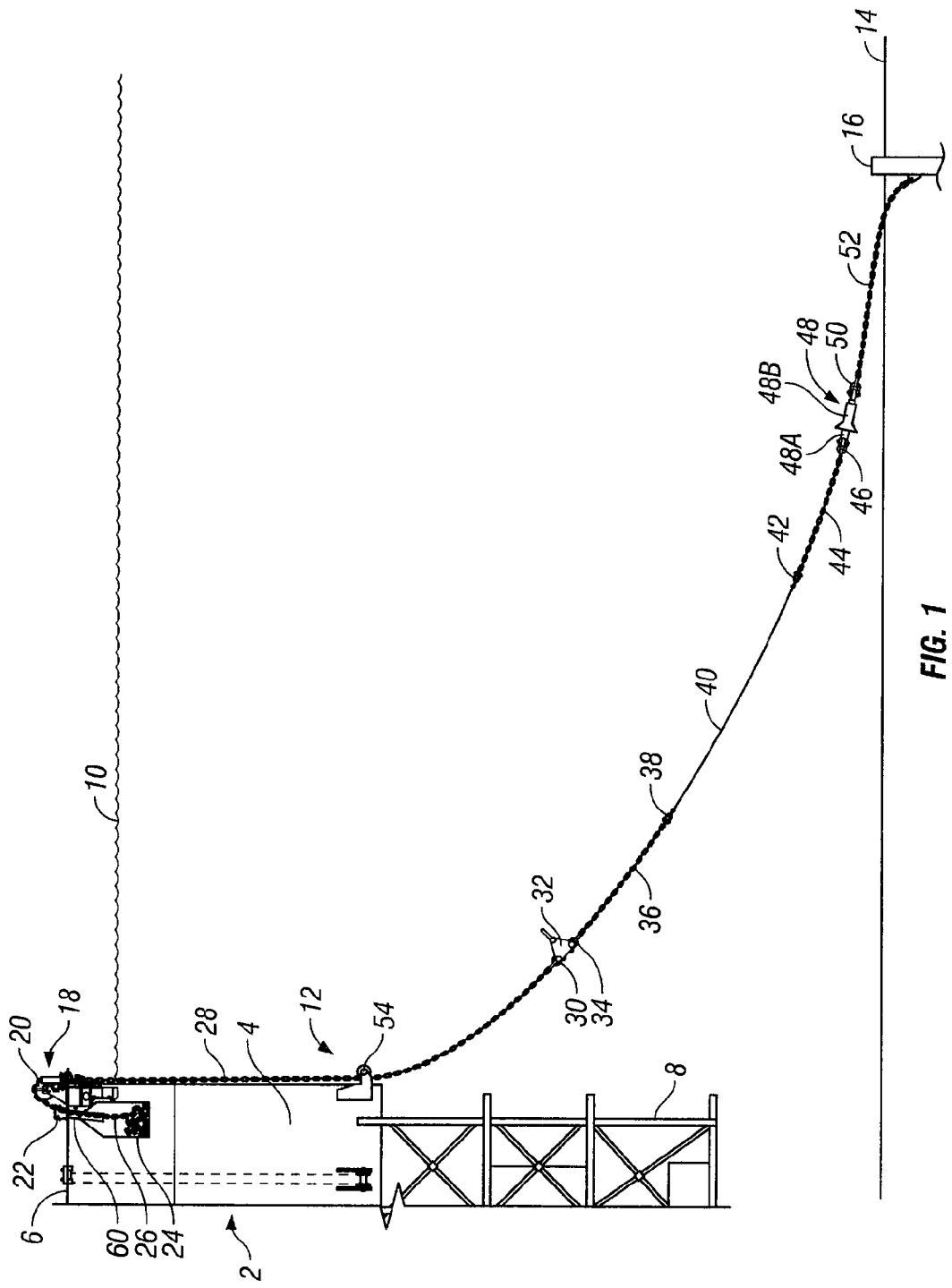
FIG. 1 is a schematic side view of an exemplary offshore platform, such as a spar, moored with a mooring line to the seabed or other connecting structure.
Figure 2:
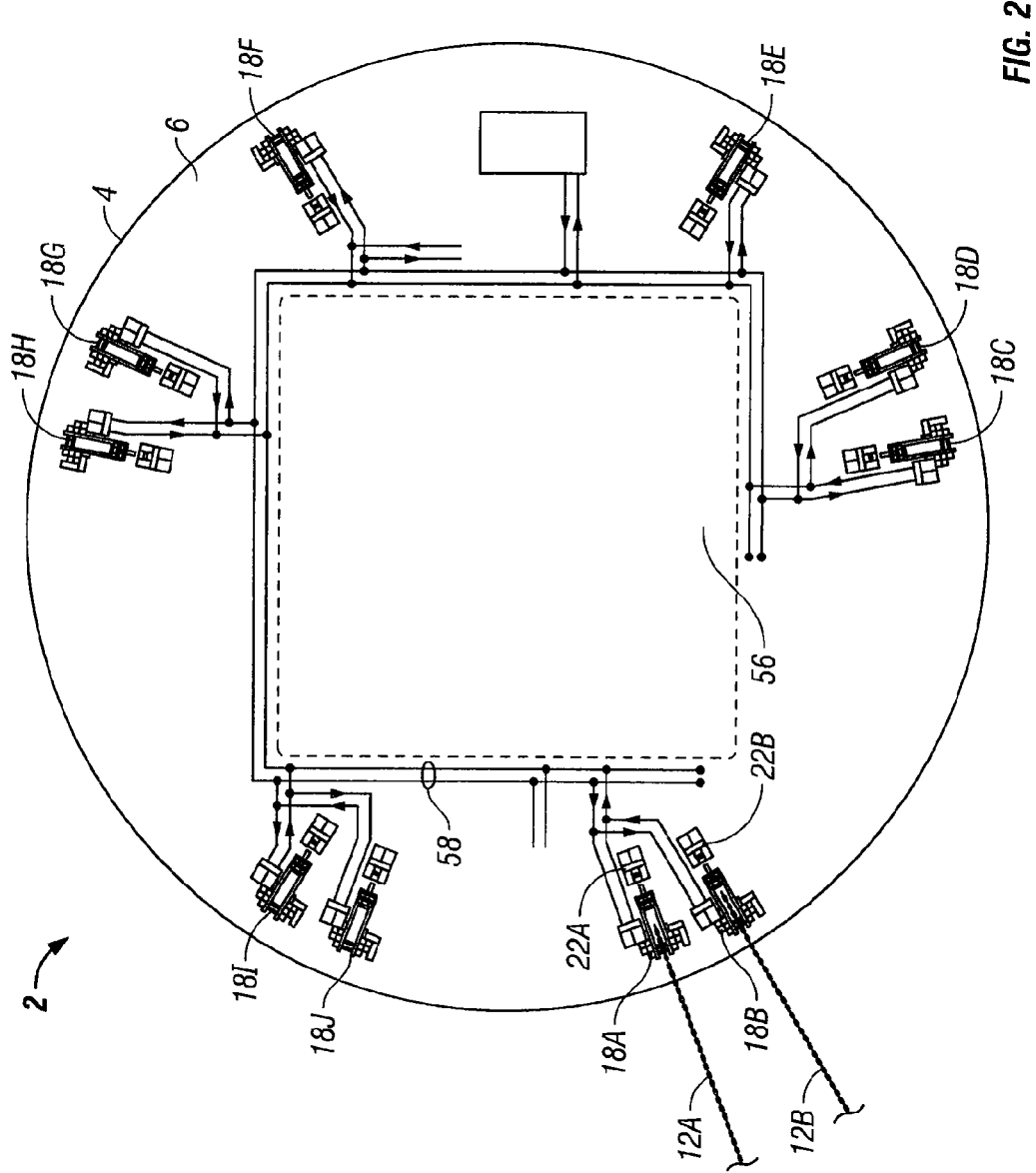
FIG. 2 is a schematic top view of the offshore platform shown in FIG. 1.
Figure 3:
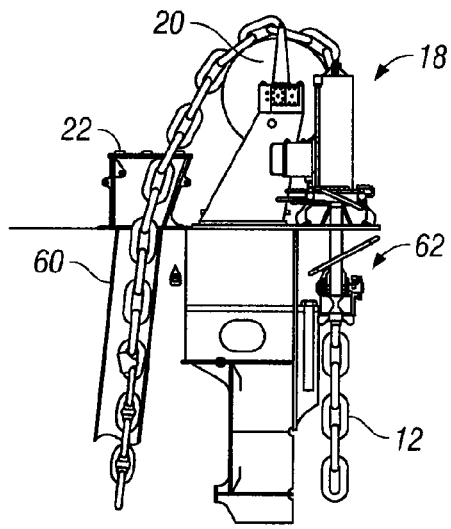
FIG. 3 is a schematic side view of a chain jack installed on the offshore platform for the mooring line.

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related, and other constraints, which may vary by specific implementation, location and from time to time. While a developer's efforts might be complex and time-consuming in an absolute sense, such efforts would be, nevertheless, a routine undertaking for those of ordinary skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims. Where appropriate, elements have been labeled with an "A", "B", and so forth to designate an element of a similar group of elements to illustrate some aspect in the description. When referring generally to such elements, the number without the letter is used. Further, such designations do not limit the number of elements that can be used for that function.

In general, the disclosure provides a method and system of coupling end-to-end at least two existing mooring lines that are already deployed from the floating platform to the seabed or other connecting structure to create a single shared line from the two lines. Each line is locked into position and disconnected from the platform structure, so that an end of each line is relatively free to be coupled to the other line through a coupling member. The shared lines then form a single looped line with both ends deployed to the subsea connections. The shared length (such as double the length of a single line if both lines were deployed the same distance) provides enough payout of line to loosen one line sufficiently, while the other line becomes correspondingly tighter using the catenary length of the tight line. In part, the line can be loosened while the other is tightened because the lines are generally in the same overall direction to the seabed, such as in a same quadrant around the platform. Thus, the lines share their available lengths to provide the necessary payout for the repairs.

Referring generally to FIGS. 1-4, an offshore platform is illustrated as a spar, with the understanding that any floating offshore platform that is moored with mooring lines is encompassed by the scope of the invention. Thus, the offshore platform will be described as a spar herein for exemplary purposes only. The spar 2 generally has a hull 4 with flotation capabilities. The hull 4 has a deck 6 with equipment mounted thereon. A lower structure 8 is used in the spar 2 to provide supporting structure for risers, heave plates, and other structures known to those with ordinary skill in the art. The spar 2 is designed to operate at a nominal water level 10 and is moored by a plurality of mooring lines 12 to the seabed 14. Generally, a pile 16 is inserted into the seabed for each mooring line. The pile 16 forms an anchoring element to which the mooring line 12 can be secured. The catenary shape of the mooring line 12 allows some flexibility in the movement of the spar 2 in response to waves and wind action.

A chain jack 18 controls tension on the mooring line 12. The chain jack 18 is generally a structure having a sheave 20 and a power unit, such as an electric motor or a hydraulic winch, for rotating and hauling in or paying out a chain portion of the mooring line 12, described in more detail herein, and thus functions as an exemplary tightening element for the respective mooring line. The chain jack 18 generally includes a chain lock 62 that can securely suspend the chain from the spar 2 when the chain jack is not operating and the inboard end of the mooring line is disconnected from the spar 2, while the mooring line awaits coupling to an adjacent mooring line or to a tail chain connected to the spar, as described herein. A portion of the mooring line 12 is stored in a chain locker 24. A chain guide 22 assists in guiding the chain from the chain jack 18 through a chain pipe 60 into the chain locker 24. The chain jacks 18 are disposed peripherally around the deck 6 of the spar 2. For example, in the embodiment shown in FIG. 2, chain jacks 18A-18J are illustrated at different radial angles around the deck 6. Each chain jack 18 is shown with a chain guide 22 leading to the respective chain lockers 24 for each chain jack. Generally, the chain jacks 18 are distributed in pairs due to the mooring lines and design criteria. Such pairs are useful in the methodology of the present invention. A plurality of power lines 58 provides power (fluid or electrical power) to the chain jacks for operation thereof. Further, a moon pool 56 is disposed generally in the center of the deck for operations on subsea wells.

Figure 4:
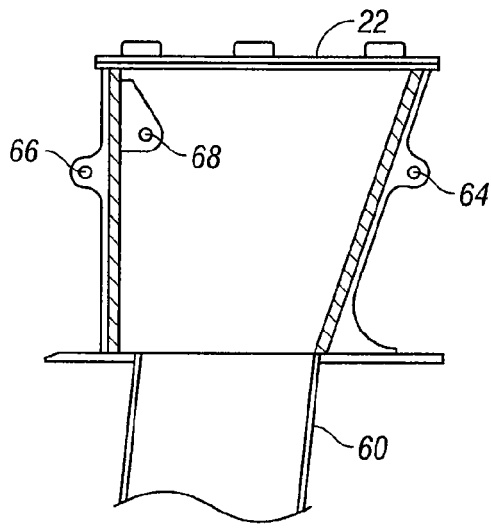
FIG. 4 is a schematic cross-sectional view of a chain guide disposed adjacent the chain jack.

The chain guide 22 can include a plurality of padeyes for different functions in the processes described herein. Referring to FIG. 4, the chain guide 22 has one or more outboard padeyes 64 that are useful for attaching a sling or other device between the padeyes and a chain portion of the mooring line. Similarly, the chain guide 22 can include one or more inboard padeyes 66, also useful for attaching slings and other devices to hold chains at different steps in the process. One or more chain guide inside padeyes 68 are disposed inside the chain guide 22.

Figure 5:
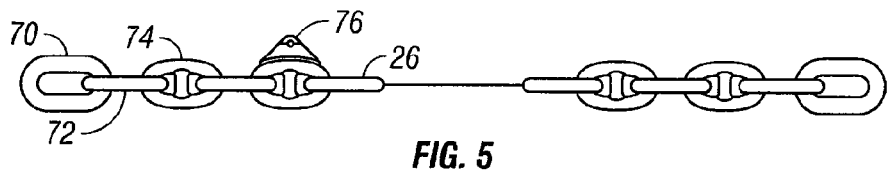
FIG. 5 is a schematic view of an exemplary tail chain, having a padeye coupled thereto.
Figure 6:
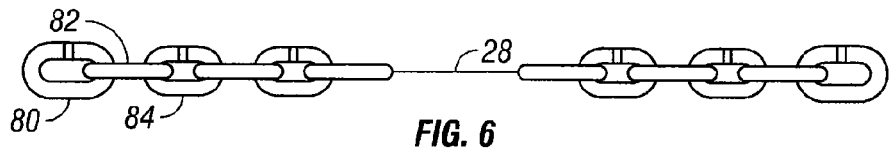
FIG. 6 is a schematic side view of an exemplary platform chain that can be coupled to the tail chain.
Figure 6A:
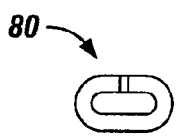
FIG. 6A is a schematic side view of an exemplary common link.
Figure 6B:
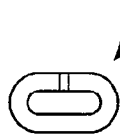
FIG. 6B is a schematic side view of an exemplary intermediately enlarged link.
Figure 6C:
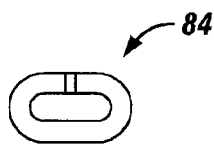
FIG. 6C is a schematic side view of an exemplary enlarged end link.

As seen particularly in FIG. 1 and FIG. 5, the mooring line 12 includes an assembled portion of a series of chains, wire rope, and associated connectors. For example, starting from the chain jack 18, a tail chain 26 is disposed at a beginning portion of the mooring line 12 on the deck 6. Generally, the tail chain 26 will be coupled to the spar, specifically to a portion of the chain locker 24 on one end of the tail chain, and to a platform chain on the other end. The tail chain 26 is shown particularly in FIG. 5. An enlarged end link 70 is suitable for coupling members, such as shackles or removable links. An intermediately enlarged link 72 is disposed between a normal sized common link 74 and the enlarged end link 70. The tail chain links can advantageously be a type of link known as a stud link having a central portion across the link to assist in keeping the links linear and from binding. The length of the tail chain 26 can vary and generally ends in the same manner in which it starts, in that the other end of the tail chain includes an enlarged end link coupled to an intermediately enlarged link coupled to the common link, where the common links comprise the majority of the chain 26. A chain padeye 76 is coupled in close proximity to an outboard end of the tail chain 26. In at least one embodiment, an exemplary and nonlimiting location considering the size and other design features for use with the chain jack 18, is on the fifth tail chain link, as shown in FIG. 5. The chain padeye 76 provides a location for coupling a sling or other fastener to hold the tail chain 26 in an appropriate position.

Referring to FIG. 1 and FIGS. 6, 6A-6C, a platform chain 28 can similarly be formed of an enlarged end link 80 coupled to an intermediately enlarged link 82 coupled to the common link 84, where the common links comprise the majority of the chain 28.

Figure 7:
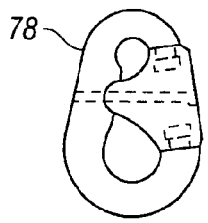
FIG. 7 is a schematic side view of an exemplary pear link.

Referring to FIG. 7, a pear link 78 functions as an exemplary coupling link that is designed to couple two ends of adjacent chains on a long term basis. In the example herein, the pear link couples an end of the tail chain 26 with an end of the platform chain 28.

Referring to FIG. 1, as referenced earlier, an inboard end of the platform chain 28 is connected to an outboard end of the tail chain 26. The platform chain 28 can form the majority portion of the chain of the mooring line 12. The platform chain 28 is generally used as the chain on which the chain jack 18 hauls in or pays out to adjust tension on the mooring line 12. The platform chain 28 is situated to extend over the side of the deck 6 and down through a fair lead 54. The fair lead 54 is coupled to the lower portion of the hull 4 and helps provide a lower center of gravity than the deck 6 for mooring the spar 2.

As the mooring line 12 progresses downward to the seabed, the platform chain 28 is coupled to a shackle 30 that is coupled to a triplate 32 coupled to a shackle 34 that in turn is coupled to a pigtail chain 36. The triplate 32 forms a structure that can be readily accessed for coupling thereto for lifting the chain and performing various service functions on the chain. The pigtail chain 36 is coupled an extended length of wire rope 40. The wire rope 40 can be a jacketed spiral strain type of wire rope. The wire rope 40 in turn is coupled to a shackle 42 that is coupled to a ground chain 44. The ground chain 44 is coupled to a shackle 46 that is coupled to a first portion 48A of a subsea mooring connector ("SMC") 48. A second portion 48B of the SMC 48 is coupled to a shackle 50 that in turn is coupled to the pile chain 52 that is coupled to the pile 16, as referenced above. The SMC 48 is designed as a removable coupling during subsea operations between a pile chain 52 attached to the pile 16 and the remainder of the mooring line 12 above the SMC. Thus, the mooring line 12 includes chain portions, a wire rope portion, various shackles, and equipment coupled thereto.

If the chain and/or coupling members, such as shackles, become damaged or otherwise need replacing, the present invention provides a method of replacing such elements. Such method includes "borrowing" a length of chain from an adjacent mooring line and extending a length of chain on a mooring line to be repaired, and then, if needed, "lending" the repaired mooring line to the second mooring line for repair of the second mooring line, collectively termed "sharing" herein.

Figure 9:
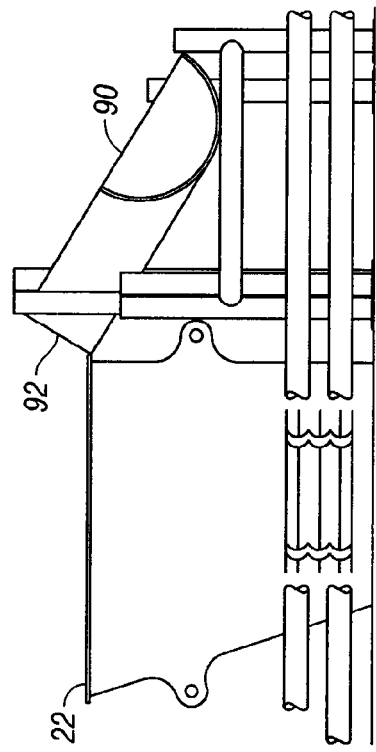
FIG. 9 is a schematic side view of the chain chute shown in FIG. 8.
Figure 10:
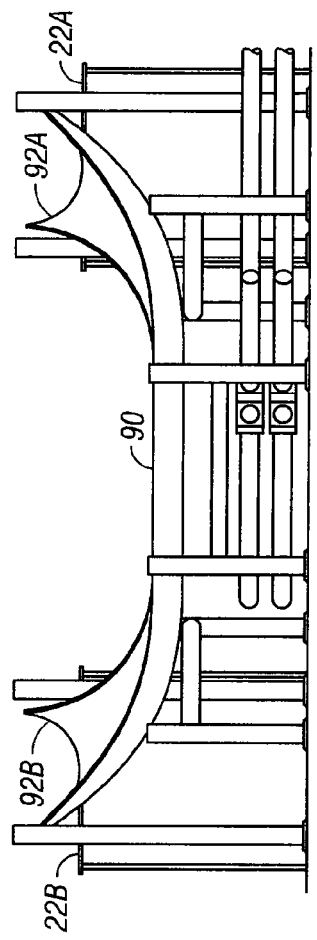
FIG. 10 is a schematic end view of the chain chute shown in FIG. 8.
Figure 8:
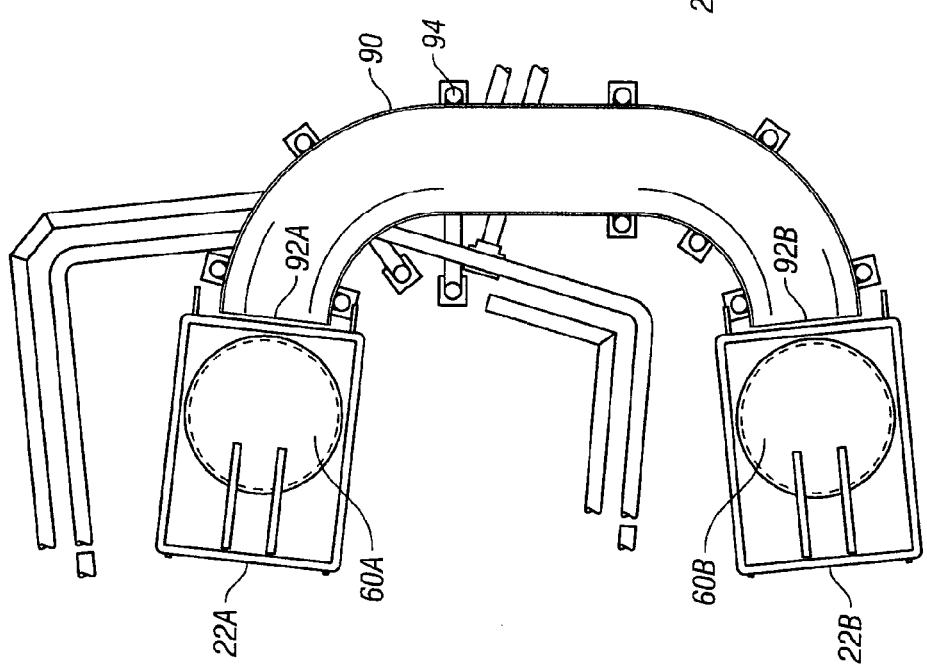
FIG. 8 is a schematic top view of an exemplary embodiment of a chain chute adjacent a pair of chain guides.

Referring to FIGS. 8-10, a chain chute 90 can be advantageously disposed to facilitate the sharing between adjacent chain jacks 18 with their respective chain guides 22 and chains 28. The chain chute functions as a holding element to hold the chains of the pair of mooring lines connected to each other, and to hold the chains when one chain is hauled in and other chain is payed out. In at least one embodiment, the chain chute 90 can be made from a 24-inch×90° long radius, extra heavy elbow that can be cut lengthwise to form both halves of the curved sections of the chute. The curved sections can be joined with a straight 24-inch diameter half-round portion to form the chute. The chute 90 can be supported by one or more supports 94 and suitable padeyes can be provided for handling and chain maneuvering. The example is only for illustrative purposes and other sizes and styles can be made. The chain chute 90 includes a first end 90A disposed adjacent to the chain guide 22A. The inside bottom of the chain chute 90 is generally disposed at or above a top of the chain guide 22 to facilitate sliding of the chain in the chute between the chain guides. Generally, the end 92A of the chain chute 90 is aligned with the chain pipe 60A of the chain guide 22A. Similarly, an end 92B of the chain chute 90 is aligned with the chain pipe 60B of the chain guide 22B.

Having provided some description of various structures and elements, the method and system disclosed herein can be generally summarized as follows:

- One or more chain chutes 90 can be installed on the spar deck 6. A first chain chute 90 can support chain sharing for mooring lines 12A and 12B from the pair of chain jacks 18A and 18B, respectively. Other chain chutes can be positioned, for example, to support chain sharing for mooring lines from chain jacks 18I and 18J. Other pairs of mooring lines can be selected sharing between such lines in like manner.
- A vessel 114, such as an anchor handling tug ("AHT"), is coupled to suitable floatover chocks to assist in positioning the spar 2.
- A pair of mooring lines 12 from either chain jacks 18A and 18B or chain jacks 18I and 18J, are slacked until the connection between platform chain 28 and tail chain 26 is above the chain guide 22.
- The connections of the platform chains 28 to the tail chains 26 on both mooring lines 12 are broken.
- The inboard ends of the platform chains 28 from the pair of mooring lines 12 are removably coupled together.
- One mooring line is slacked by paying out the mooring line, while the other mooring line is hauled in to share chain and increase the available working length of the slacked mooring line.
- The vessel 114 recovers the platform chain 28 on the slacked mooring line and performs repairs, such as removal and replacement of upper shackles 30, 34, and triplate 32, as appropriate.
- The vessel 114 inserts a temporary "insert" chain 128 between the platform chain 28 and the pigtail chain 36.
- The vessel 114 changes out lower shackles 38, 42, 46 as appropriate.
- The vessel 114 recovers the insert chain 128 and removes it from the mooring line 12.
- The vessel 114 connects new shackles and deploys the platform chain 28.
- The slacked, repaired mooring line is hauled in while the other mooring line from the other chain jack is slacked to make similar repairs in like manner. The insert chain is added to the other mooring line, shackles are changed out, and the insert chain is removed.
- The slacked second mooring line is hauled in while the first mooring line is slacked until the removable connection between the platform chains is disposed on the chain chute.
- The platform chains are disconnected and reconnected to their respective tail chains.
- The mooring lines are adjusted to operational condition.
- The exemplary operation is repeated for other pairs of mooring lines.

Additionally, some preparatory steps are useful prior to actually effecting the chain sharing. Some elements, devices, and equipment will be referenced generally, while further discussion will be made below regarding FIGS. 11-30. To facilitate the sharing between adjacent mooring lines, the chain chute can be formed, or if already formed, can be disposed adjacent a pair of chain guides (as shown in FIGS. 8-10). An air tugger or other powered winch having a quantity of wire rope or other chain disposed on a drum is mounted on a rotating foundation just inboard of the relevant chain guide. Various equipment, including shackles, wire slings, chain hoists, snatch blocks, and additional wire and wire clamps, are obtained for making up special purpose slings as required. A detachable LLLC link or other easily detachable link as a coupling element is obtained for connecting inboard portions of the platform chains for chain sharing, as described herein. Additionally, suitable guards and scaffolding can be installed over the chain jack hydraulic lines and power lines. An anchor handling tug vessel described below can be loaded with, if not already on board, a quantity of studlink chain to be used as an insert chain. The insert chain allows hangoff, disconnection, and reconnection of the SMC without the vessel's work wire clashing with the other adjacent mooring lines. Additionally, a plurality of shackles, such as bow shackles, can be provided to connect the insert chain to the platform chains and pigtail chains described below. A chain hoist can be rigged from an overhead padeye located above the chain guide. Various marker buoys can also be obtained for marking the location of ground chains and other subsea portions of the mooring line.

In general, the spar should be positioned at the center of the well pattern. The main and shared platform chain lengths are used to allow the platform and pigtail chains to be loaded on the deck of the vessel used to make the repairs to the mooring lines. When slacking mooring lines on one side of the spar, mooring lines for the opposite side of the spar may be slacked by a suitable distance depending on environmental conditions and the response of the spar during the chain sharing operations. The slacking of opposite mooring lines can occur before the chain sharing on the first line, after the slacking of the first line but prior to the second line of the pair, or in some step sequence where the lines being repaired and the opposite lines are alternately slacked by some intermediate portion.

To prepare the mooring line for shackle changeout operations, a vessel can rig a sling with its submersible marker buoy. An ROV can be deployed with the sling and buoy to the first mooring line for the shackle changeout operation, as required. The ROV feeds one eye of the sling through the ground chain adjacent to pile inboard (that is, in the direction of the spar) of the SMC and rigs up the sling with the submersible buoy and is recovered to the surface. The operation is repeated for the second line of the pair.

Having made some preparatory steps, the method of sharing can be described in more detail below. FIGS. 11-30 reference a series of illustrated procedures that are exemplary for at least one embodiment of a method of sharing mooring line lengths for changing out one or more elements in a designated mooring line, adding or removing a length of mooring line, or other adjustments as may be appropriate (broadly referred to herein as "repair" or "repairing"). To share and repair the mooring lines, an arbitrary pair of mooring lines 12A, 12B is illustrated below with the understanding that other pairs of mooring lines could have been selected and the description herein uses such pair only as an illustration. Where appropriate to distinguish between which mooring line is being described below, references to "A" and "B" for the particular element are made. For purposes of illustration only and without limitation of the method and system of sharing mooring lines, the mooring line 12A is selected to be repaired first and then mooring line 12B is selected to be repaired. In actuality, a one of the mooring lines of the pair may need repair and the other mooring line may continue to be used without repair.

Figure 11:
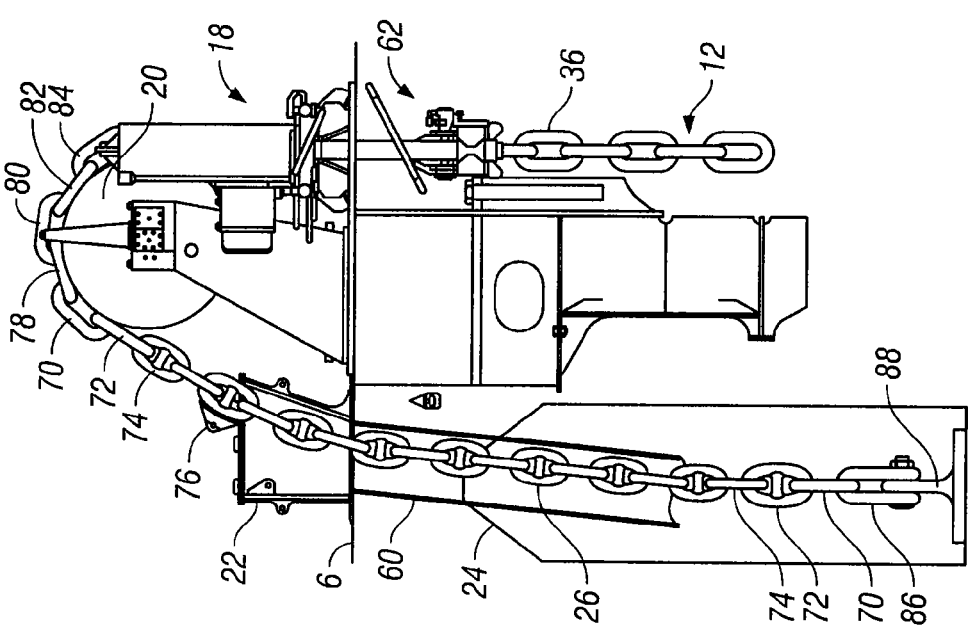
FIG. 11 is a schematic side view of a chain jack supporting a platform chain, the chain jack being adjacent a chain guide with a chain tube providing access to a chain locker with a tail chain coupled thereto.

Referring to FIG. 11, a platform chain 28 is coupled to a tail chain 26. As described in reference to FIG. 5, the tail chain 26 can include an enlarged end link 70, suitable for allowing shackles and other devices to pass therethrough for coupling the tail chain to supporting structures or an adjacent chain, an intermediate enlarged link 72, and common link 74. The chain padeye 76 is coupled a few links away from the end of the tail chain 26 that is coupled to the platform chain 28. The end link 70 of the tail chain 26 that is distal from the platform chain 28 is coupled to a shackle 86 that is coupled to a locker padeye 88 that in turn is coupled to the structure of the spar 2. Thus, under normal operating conditions, the mooring line 12 is connected to the structure of the spar 2 on the inboard end of the tail chain 26.

In operation, the platform chain 28 of the mooring line 12 is paid out with the chain jack 18. Once the pear link 78 that connects the platform chain 28 with the tail chain 26 is available inside the chain guide 22, the chain jack 18 is stopped. The chain jack then slowly slacks the mooring line 12 to position the chain padeye 76 close to the padeye 68 inside the chain guide 22, and the chain jack 18 is stopped.

Figure 12:
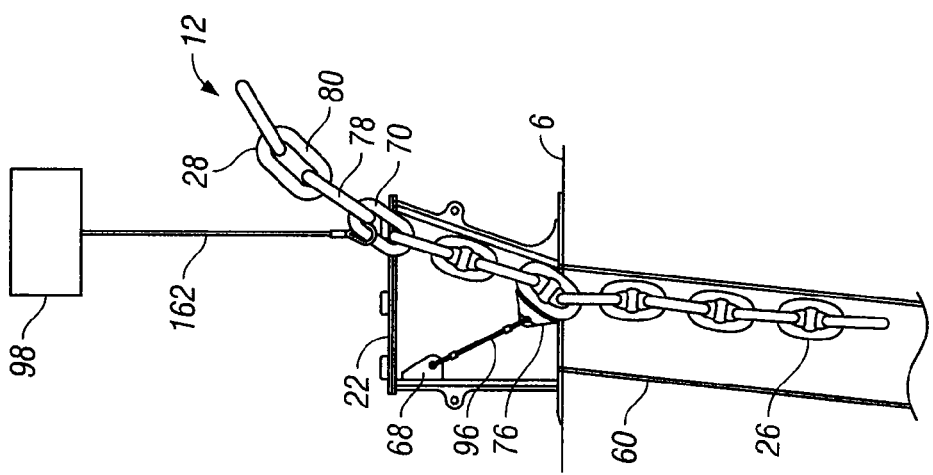
FIG. 12 is a schematic cross-sectional view of a suspended tail chain.

Referring to FIG. 12, using shackles and a short sling 96, the chain padeye 76 is secured to the padeye 68 on the inside of the chain guide 22. The sling 96 supports the chain padeye 76 in the chain guide 22. Once the sling 96 is connected to the chain padeye 76, the mooring line 12 and specifically the platform chain 28 portion of the mooring line 12 is slowly hauled in until the sling 96 takes the load off of the tail chain 26 in the chain locker 24, so that the sling is suspending the tail chain below the chain padeye 76. The platform chain 28 outboard of the turndown sheave 20, shown in FIG. 11, is securely locked in the chain lock 62.

Figure 13:
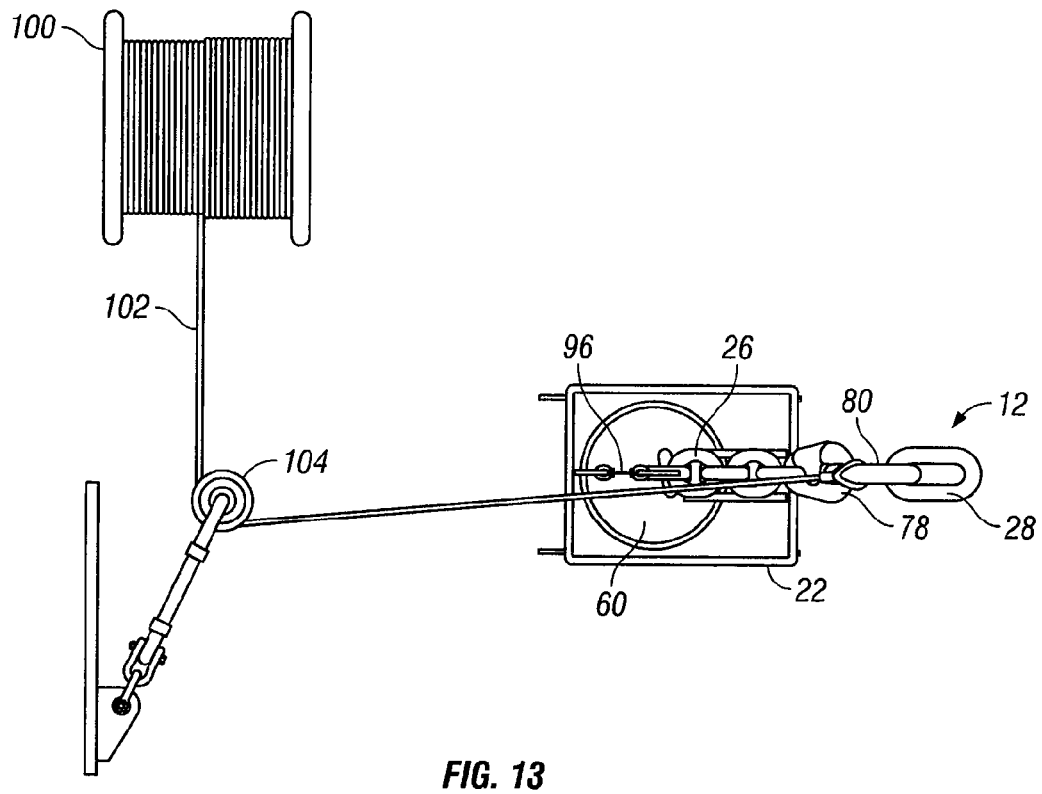
FIG. 13 is a schematic top view of an air tugger coupled through a tugger wire to the platform chain.

Referring to FIGS. 12 and 13, a chain hoist 98 can be rigged from over the chain guide 22 and connected with another sling into the tail chain end link 70. An air tugger 100 can be coupled to the platform chain 28 just above the pear link 78, such as on the end link 80. The tugger wire 102 from the air tugger 100 can be led through a suitable snatch block 104 to pull the platform chain 28 inboard from a position above the pear link 78. The platform chain 28 is slowly hauled in with the chain jack 18 (shown in FIG. 11), while hauling in the air tugger wire 102 and adjusting the chain hoist 98 to gain slack at the pear link 78. Once the mooring line 12 has been slacked sufficiently, the chain jack 18 is stopped. The pear link 78 can be decoupled from the tail chain 26 and platform chain 28 and set aside.

Figure 14:
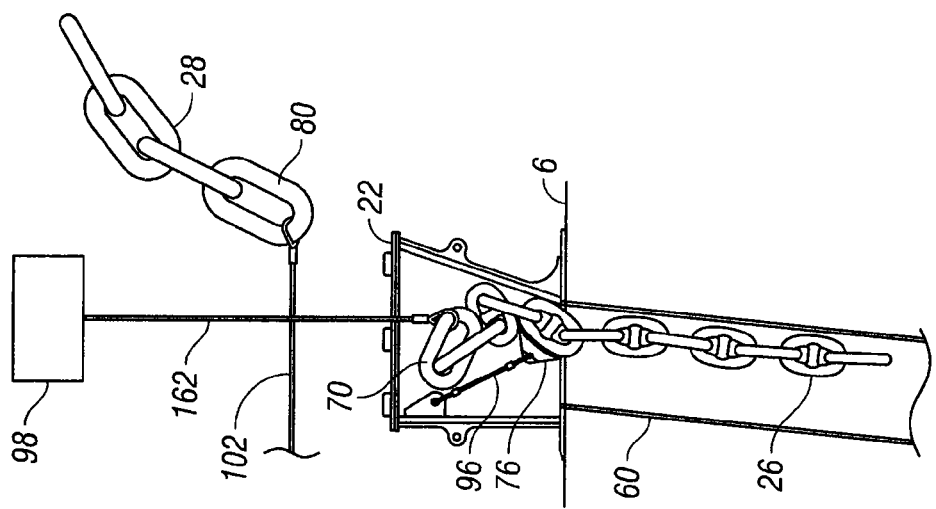
FIG. 14 is a schematic cross-sectional view of the platform chain disconnected from the suspended tail chain.

Referring to FIG. 14, the tail chain 26 is supported by the sling 96, and the chain hoist 98 is adjusted to lower the outboard end link 70 of the tail chain into the chain guide 22. Thus, the end link 70 of the tail chain 26 above the chain padeye 76 is sitting in the chain guide 22. The end link 70 is secured to the chain padeye 76 inside the chain guide 22 and the hoist 98 is disconnected. The tugger wire 102 is coupled to the inboard end link 80 of the platform chain 28, and the pear link 78 has been removed and set aside.

Figure 15:
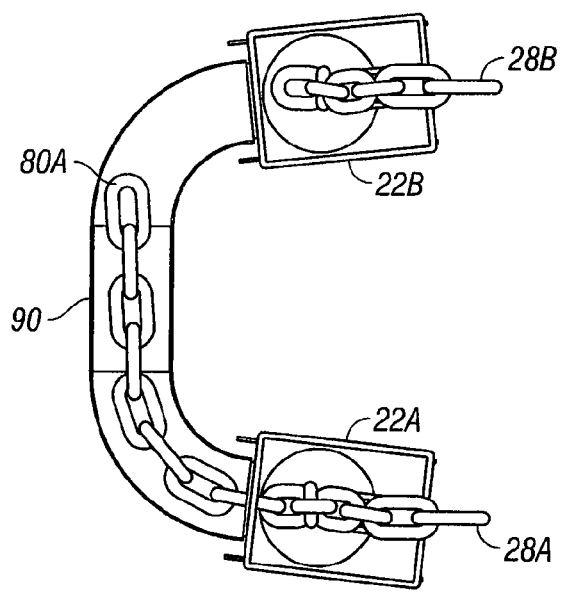
FIG. 15 is a schematic top view of a platform chain disposed in a chain chute awaiting connection to an adjacent platform chain.

Referring to FIG. 15, the platform chain 28 (such as chain 28A) is hauled in until the platform chain 28A, particularly the end link 80A, is disposed in the chute 90, using the air tugger 100 and/or chain hoist 98 (shown in FIGS. 12 and 13) to handle the chain.

Figure 16:
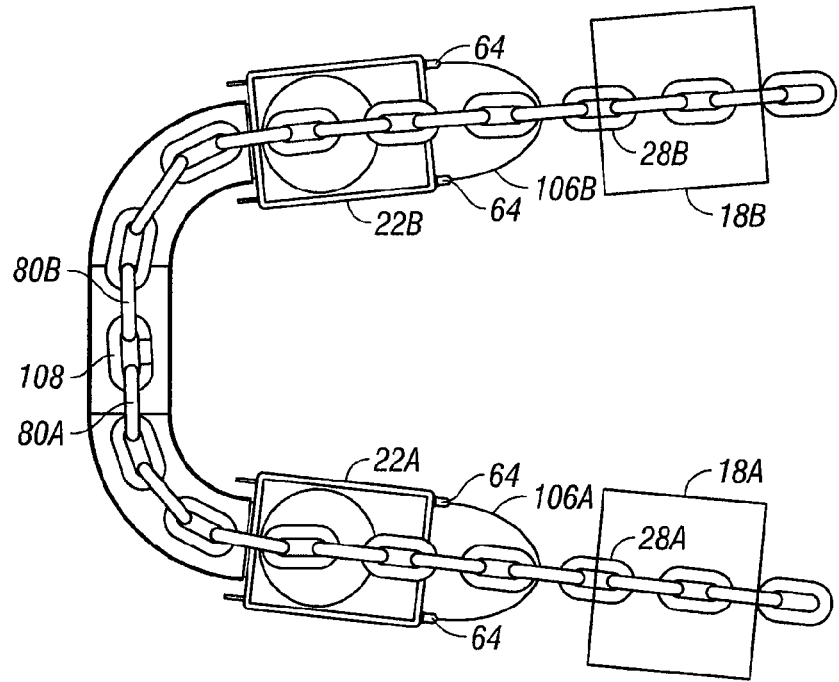
FIG. 16 is a schematic top view of the shared platform chains being coupled by a link and disposed in the chain chute.

Referring to FIG. 16, the platform chain 28A is secured to the outboard padeye 64 of the chain guide using one or more shackles and wire slings 106A. The air tugger is disconnected from the platform chain 28A.

The steps are then repeated for the second platform chain 28B. The second platform chain 28B is disconnected from its respective tail chain and the tail chain suspended by a padeye in the chain guide 22B. The end link 80B of the platform chain 28B is pulled in and a sling 106B is fastened to the outboard padeye 64 on the chain guide 22B. The air tugger can be similarly disconnected. Thus, at this time, both tail chains are disconnected from their respective platform chains 28A, 28B and each platform chain is secured and tension taken by the slings 106A, 106B being coupled to the chain guide 22A, 22B, respectively. The chain lock 62 on the chain jack 18 (shown in FIG. 3) is engaged to secure the platform chains to the spar 2. The detachable link 108 is used to couple together the end links 80A, 80B of the platform chains 28A, 28B, respectively.

The chains 28A and 28B are now effectively a continuous chain with each remaining end secured to the seabed and the lengths of each formerly separate chain being available for sharing with the other formerly separate chain. Because of the significant chain lengths needed for repair operations, such as lifting the chain to a floating vessel, the present invention allows sharing of pairs of chains to obtain additional effective lengths, without generally necessitating additional lengths of platform chain stored in the spar for each mooring line.

Both platform chains 28A, 28B are hauled in enough to gain slack inboard of the securing slings, and the security slings are disconnected. If necessary, the air tugger can be coupled to a platform chain to pull in the platform chain and take the load off the sling in order to disconnect the sling.

Figure 17:
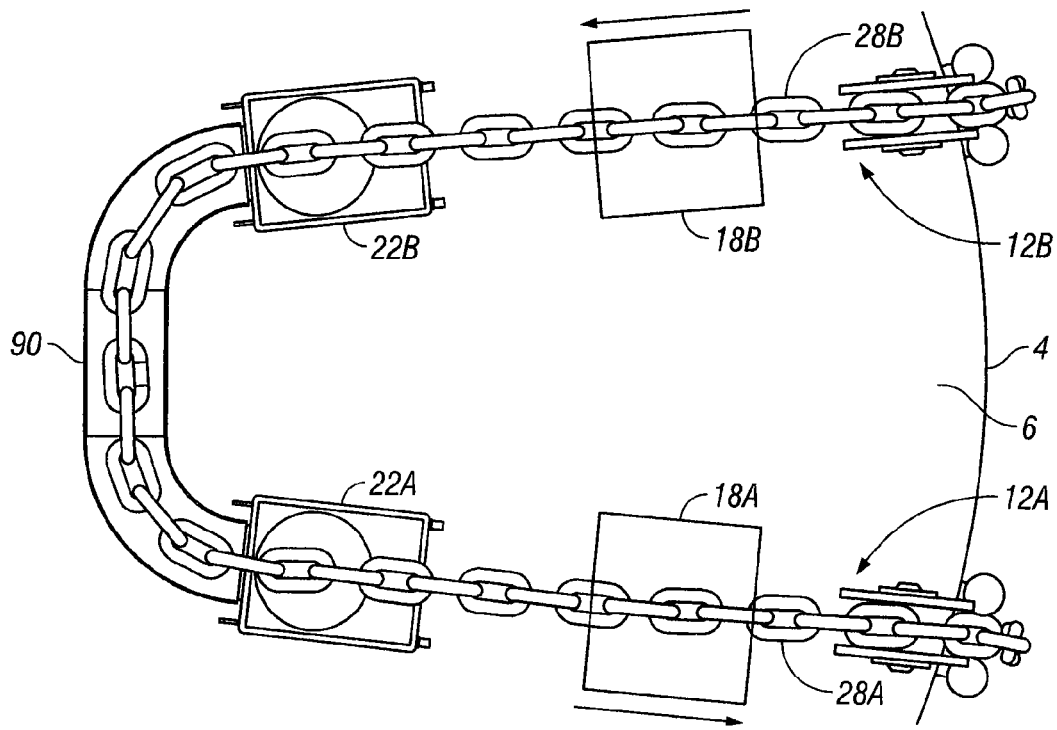

Referring to FIG. 17, the platform chain 28B is hauled in through the chain jack 18B and the platform chain 28A is paid out in an offsetting manner through the chain jack 18A. Thus, the mooring line 12A is ready to be repaired.

Figure 18:
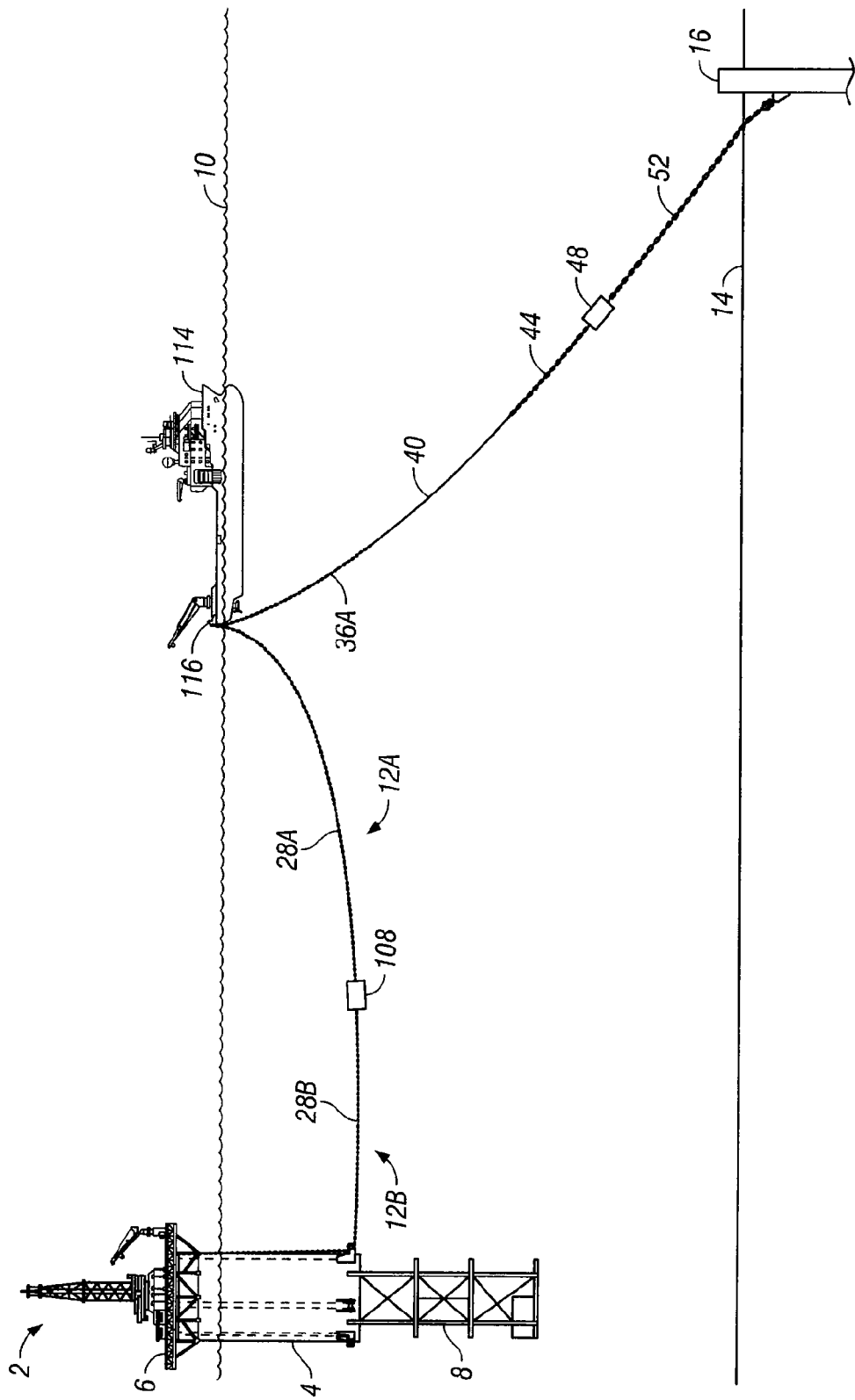
FIG. 18 is a schematic elevational view of the spar and the mooring line being repaired by a vessel, such as an air handling tug.
Figure 19:
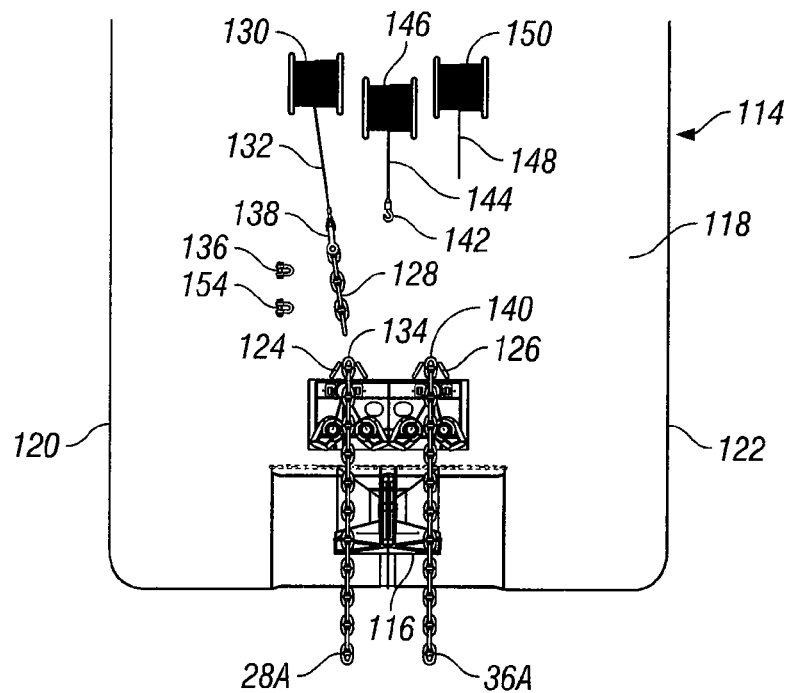
FIG. 19 is a schematic top view of the deck portion of the vessel, showing suspended chains and working winches to manipulate the chains.

Referring to FIGS. 18 and 19, the vessel 114 retrieves the platform chain 28A and pigtail chain 36A onto the back deck 118 of the vessel. Other vessels (not shown) may be useful for assisting in various steps of the chain sharing process described herein, such as by holding portions of the mooring line, while the first vessel changes out other portions of the mooring line, such as shackles. Thus, the reference to the vessel 114 is intended to mean a single vessel or a plurality of vessels working together to accomplish the tasks. The platform chain 28A is secured to the vessel 114 through a chain lock 124 (also known as "shark jaws") on the port side 120 of the vessel 114. Similarly, the pigtail chain 36A is secured on the starboard side 122 in a corresponding chain lock 126 (or "shark jaws"). The existing shackles 40, 34 and triplate 32 (shown in FIG. 1) are removed, replaced if necessary, marked, and stored. A temporary insert chain 128 is paid out from a winch 130 on the port side of the vessel to an outboard end 134 of the platform chain 28A that is secured on the deck 118 by the shark jaws 124. The insert chain 128 functions as a chain extension between the platform and pigtail chains. The insert chain 128 is coupled to the platform chain 28A with a shackle 136. A load from the winch 130 using the winch wire 132 is applied to the insert chain 128 to pull tension on the insert chain and the platform chain 28A coupled thereto. The shark jaws 124 are released and the insert chain 128 with the platform chain 28A is deployed.

When the insert chain is deployed so that the inboard end 138 of the insert chain 128 is on the deck 118, the port shark jaws 124 can be reengaged. The on deck, inboard end 138 of the insert chain is disconnected from the wire 132 of the port winch 130. The inboard end 138 of the insert chain is then connected to the pigtail chain 36A using a shackle 154.

Figure 20:
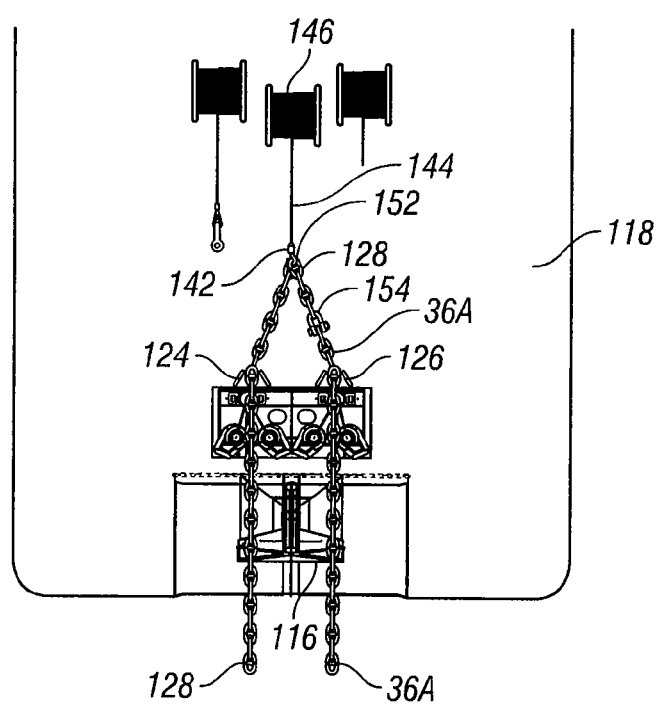
FIG. 20 is a schematic top view of the vessel deck, showing chains coupled to each other.
Figure 21:
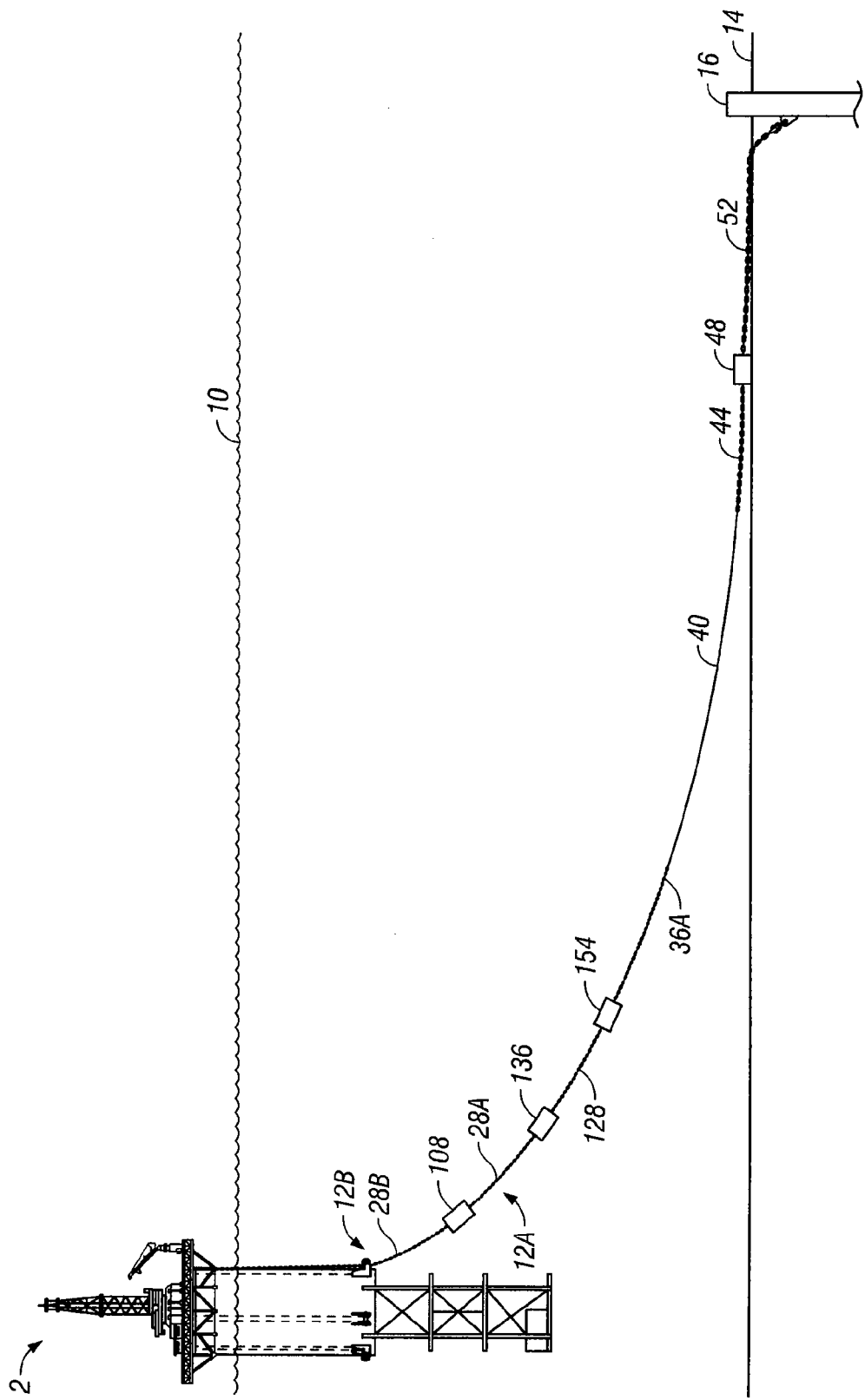
FIG. 21 is a schematic side elevational view of the mooring line with upper elements of the mooring line replaced.

Referring to FIGS. 20 and 21, a link 152 along the insert chain 128 above the shackle 154 is coupled with a J-hook 142 and the link is marked. A load is taken on the J-hook 142 using a wire 144 from a winch 146 to put tension on the insert chain 128 and the pigtail chain 36A. When the load is taken, the shark jaws 124 holding the insert chain 128 and the shark jaws 126 holding the pigtail chain 36A are released. The J-hook 142 is then launched over the stern roller 116 and the mooring line is deployed. Once the mooring line load is off the J-hook 142, the J-hook is released and retrieved.

The vessel 114 maneuvers to recover the ground chain 44 and disconnect the ground chain from the SMC 48 to change out the lower shackles and any other associated components shown in FIG. 1. The ground chain 44 with first portion 48A of the SMC 48 is disconnected in the customary manner from the second portion 48B of the SMC, the elements being shown in FIG. 1. The ground chain 44 is recovered using the J-hook 142 from the vessel 114 to the vessel deck, and the shackles 38, 42 and 46 shown in FIG. 1 can be replaced, as appropriate.

After repairs, the ground chain 44 and attached components are lowered and the first and second portions of the SMC 48 are reconnected. Further repairs, if appropriate, can be made to the lower shackle 50 coupling the SMC 48 with the pile chain 52, shown in FIG. 1. A chain table (not shown) hung from the top of the pile 16 can hold the pile chain 52 securely with ROV hydraulically operated pinchers or fingers so that the shackle 50 can be cut with an ROV saw, shackle pieces removed, and an H-link installed to reconnect the SMC 48 to the pile chain.

Figure 22:
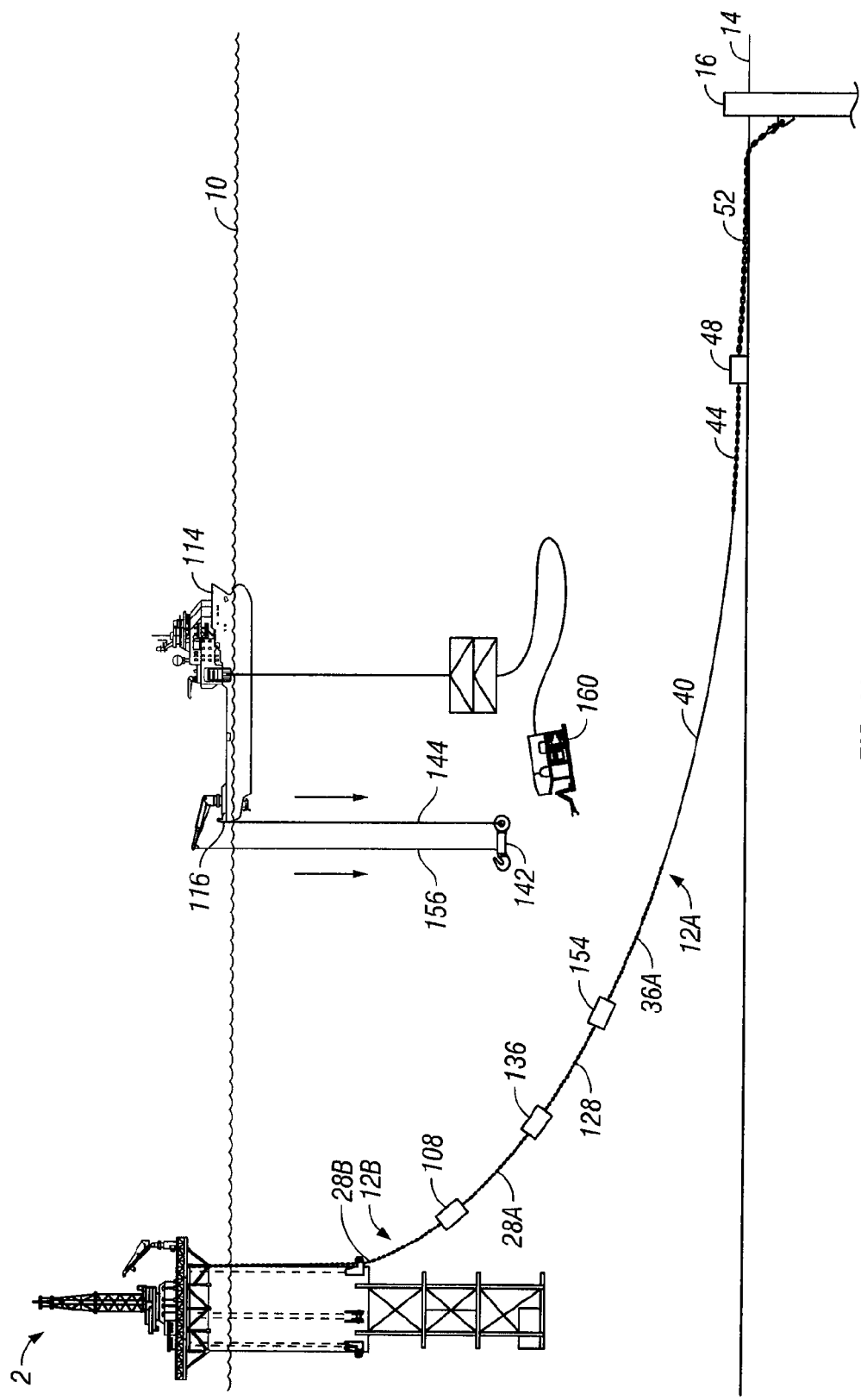
FIG. 22 is a schematic side elevational view of the vessel lowering a hook to retrieve a lower portion of the mooring line to replace lower elements.
Figure 23:
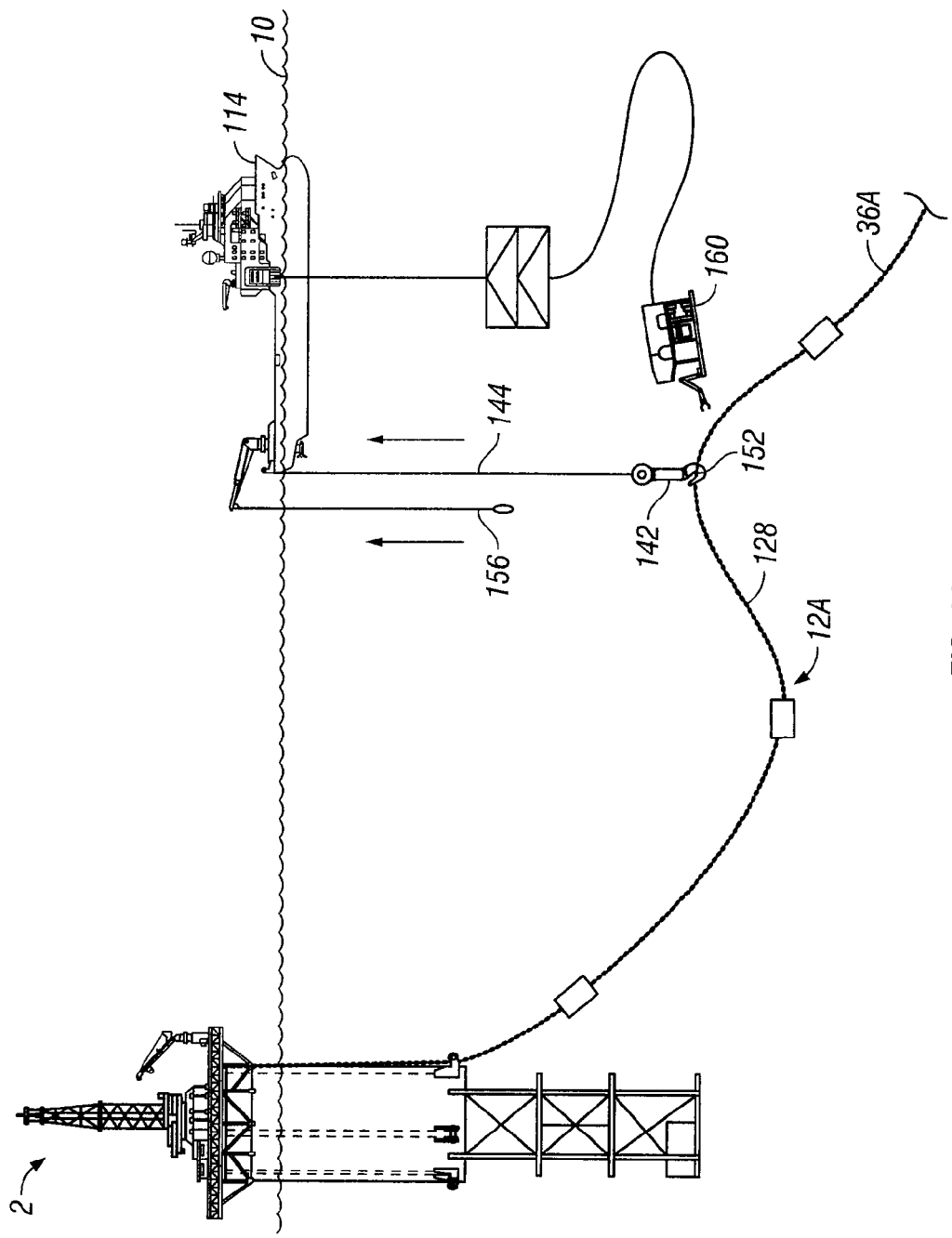
FIG. 23 is a schematic side elevational view of the vessel, lifting the mooring line.

Referring to FIGS. 22 and 23, the vessel 114 maneuvers toward the spar 2. The vessel 114 can deploy the J-hook 142 with a wire 144 coupled to the winch 146, shown in FIG. 20. Additionally, a separate wire 156 from an A-frame on the vessel 114 can be coupled to an orientation padeye on the J-hook 142 to control the angle of the J-hook. The J-hook can hook into the insert chain 128, preferably at the marked link 152, referenced in FIG. 20, just above the shackle 154 connecting the pigtail chain 36A with the insert chain 128. To assist the retrieval, an ROV 160 can also be deployed from the vessel 114 or from a second separate vessel (not shown). Once engaged with the insert chain 128, the ROV can disconnect the wire 156 from the J-hook 142 and the wire 144 is hauled in on the vessel 114 and the mooring line 12A lifted.

Figure 24:
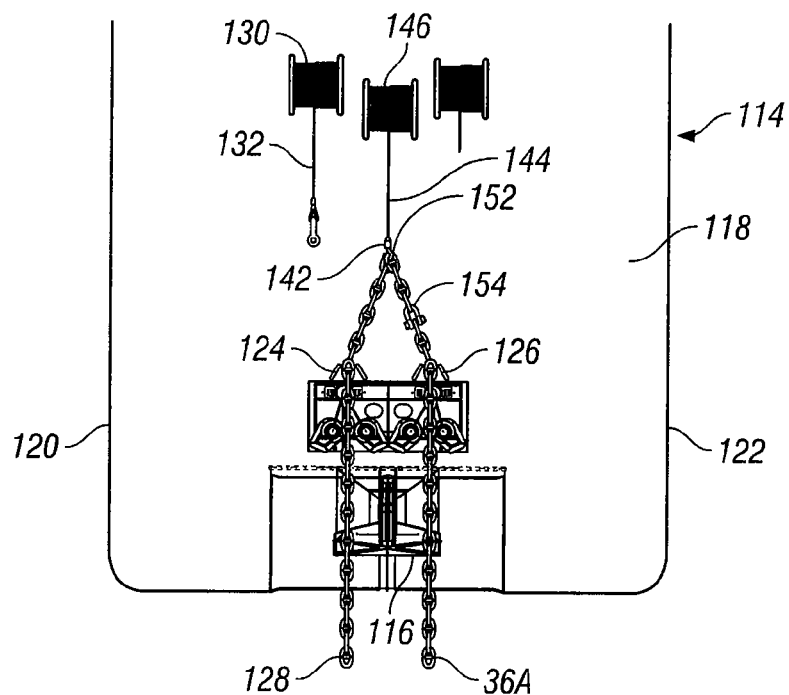
FIG. 24 is a schematic top view of the vessel deck, showing an outboard portion of the insert chain coupled to a pigtail chain.

Referring to FIG. 24, the vessel 114 retrieves the chain onto the deck 118. The vessel 114 maneuvers to situate the insert chain 128 to the port side 120 and the pigtail chain 36A to the starboard side 122. The insert chain 128 can be held in place with the port shark jaws 124. The pigtail chain 36A can be held in place by the starboard shark jaws 126. The shackle 154 that coupled the insert chain 128 with the pigtail chain 36A is disposed to the starboard side of the J-hook 142 nearest the pigtail chain 36A. Once the chains are secured in their respective shark jaws, the shackle 154 can be removed.

Figure 25:
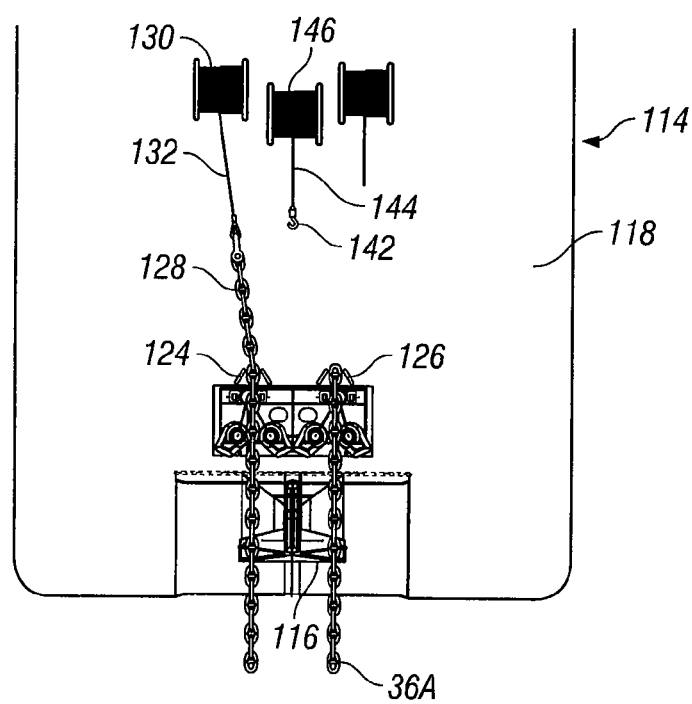
FIG. 25 is a schematic top view of the deck showing the insert chain disconnected from the pigtail chain and the insert chain hauled in to access the platform chain.
Figure 26:
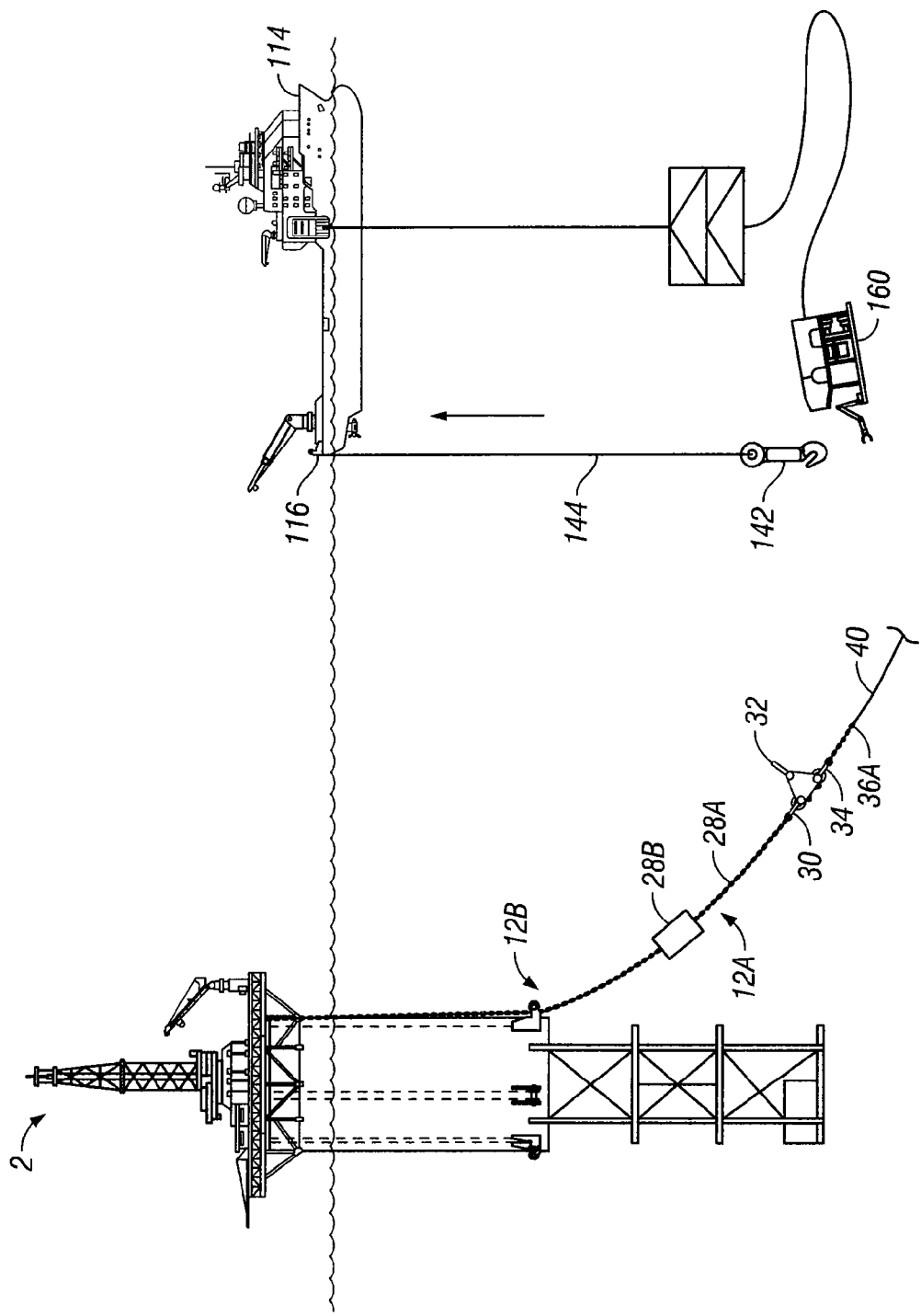
FIG. 26 is a schematic side elevational view of the pigtail chain coupled with the platform chain and lowered from the vessel into the sea.

Referring to FIGS. 25 and 26 and portions of FIG. 19 described earlier, the insert chain 128 can be connected to the wire 132 of the port winch 130. After a load is taken by the wire 132 on the insert chain 128, the port shark jaws 124 can be disengaged and the insert chain 128 hauled in and spooled on the drum of the port winch 130. When the shackle 136, shown in FIG. 19 connecting the platform chain 28A to the insert chain 128, is forward of the shark jaws 124, the winch 130 is stopped and the shark jaws 124 reengaged on the platform chain 28A and the shackle 136 is removed. The triplate 32 and adjacent shackles 30, 34, shown in FIG. 1, are connected between the platform chain 28A and the pigtail chain 36A. The J-hook 142 engages the platform chain 28A just above the shackle 30 and the associated triplate 32. The load is taken on the J-hook 142 from the wire 144 and the shark jaw 124 released. The J-hook 142 and platform chain 28A with the pigtail chain 36A are launched over the stern roller 116. The weight of the mooring line 12A is removed from the J-hook 142 after lowering the mooring line, and the J-hook is disengaged. The ROV 160 can assist, as required.

With the mooring line 12A being repaired, the operation switches to the mooring line 12B. In the above example, the mooring line 12B shared its platform chain 28B to make the repairs to the mooring line 12A. The mooring line 12A, whose shackle and any other components have been repaired, now shares its platform chain 28A with the mooring line 12B.

Figure 27:
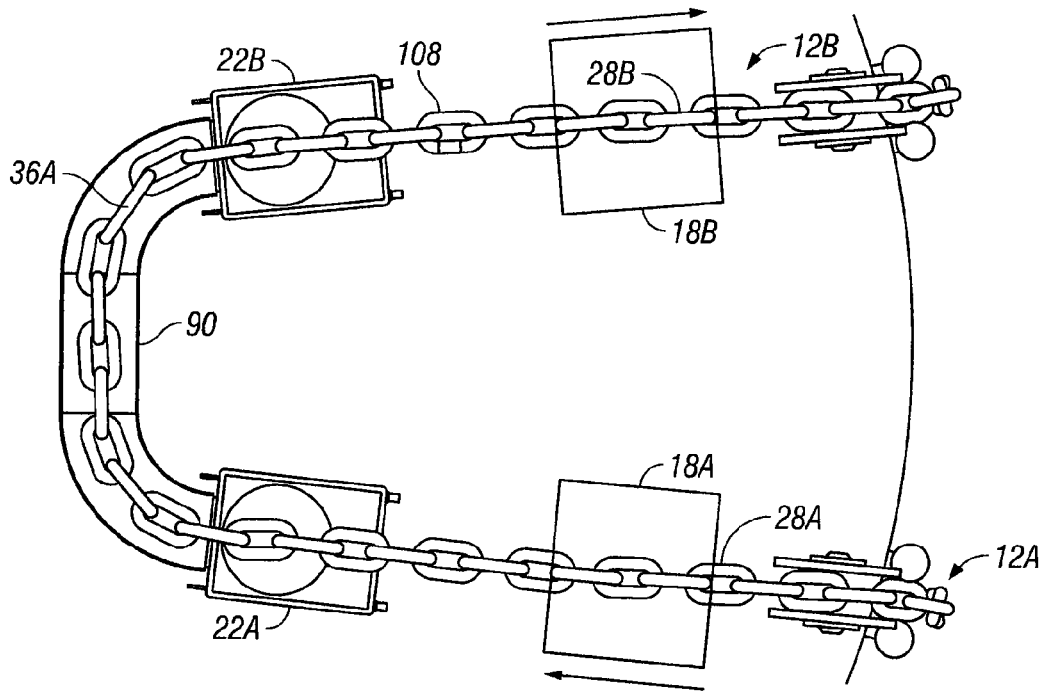
FIG. 27 is a schematic top view, illustrating hauling in the first mooring line and providing slack to the second mooring line of the pair of mooring lines.

Referring to FIG. 27, the combined platform chains 28A, 28B can be shifted by the chain jacks 18A, 18B, for example, one chain stroke at a time, so that as the platform chain 28B of the mooring line 12B is paid out, the platform chain 28A of the mooring line 12A is hauled in. Once the shared platform chain 28B is sufficiently deployed, the vessel 114 recovers the platform chain 28B and corresponding pigtail chain, inserts the insert chain 128, changes out lower shackles and other components as appropriate, removes the insert chain, changes out the upper shackles and any other components, and repairs the mooring line 12B, as was described above for the mooring line 12A. The order of change out between the lower and upper shackles and whether all of the shackles are changed out can vary on a case by case basis.

Figure 28:
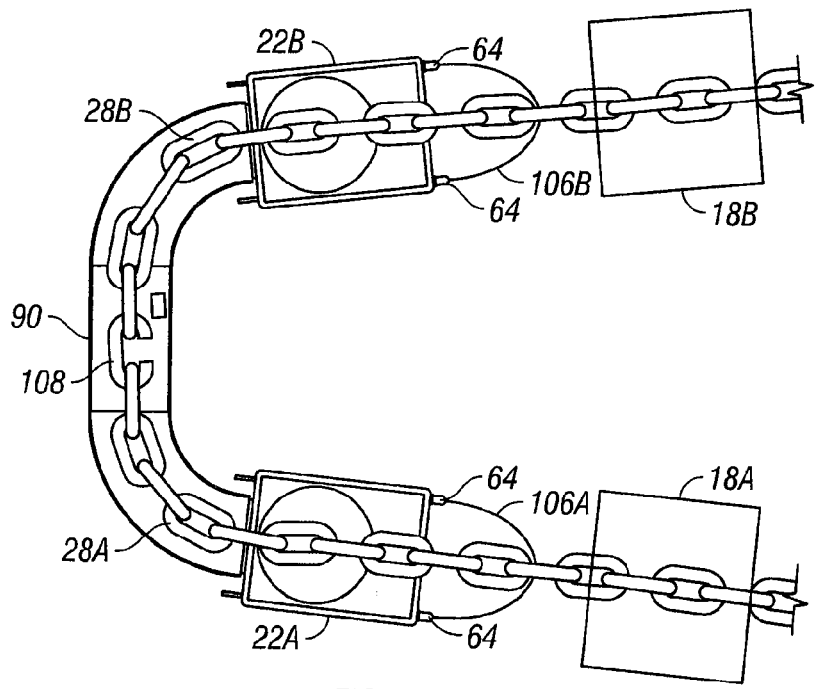
FIG. 28 is a schematic top view, illustrating the recentering of the link between the two platform chains on the chain chute for disconnecting the platform chains.

Referring to FIG. 28, after the mooring line 12B is repaired, the shared platform chain 28B is hauled in, and the platform chain 28A is paid out until the detachable link 108 is disposed generally in the middle of the chain chute 90. A securing sling, such as the sling 106B, is inserted through one of the platform chains, such as the platform chain 28B, and connected to the outboard padeyes 64 on the respective chain guide, such as the chain guide 22B. An air tugger 100, shown in FIG. 13, is coupled to the opposite platform chain, such as platform chain 28A, on the chain chute 90 and the platform chain 28A pulled toward the platform chain 28B to allow the platform chain 28B to pay out slightly until the securing sling 106B carries the weight of the platform chain 28B inboard of the chain jack 18B.

A second securing sling 106A is inserted through the platform chain 28A and connected to the outboard padeyes 64 of the chain guide 22A. The chain jack 18A is slacked just enough to allow the securing sling 106A take the weight of the platform chain 28A inboard of the chain jack 18A. With both platform chains 28A, 28B secured to the chain guides 22A, 22B by the slings 106A, 106B and the slack inboard of their respective chain jacks, the detachable link 108 can be disconnected.

Figure 30:
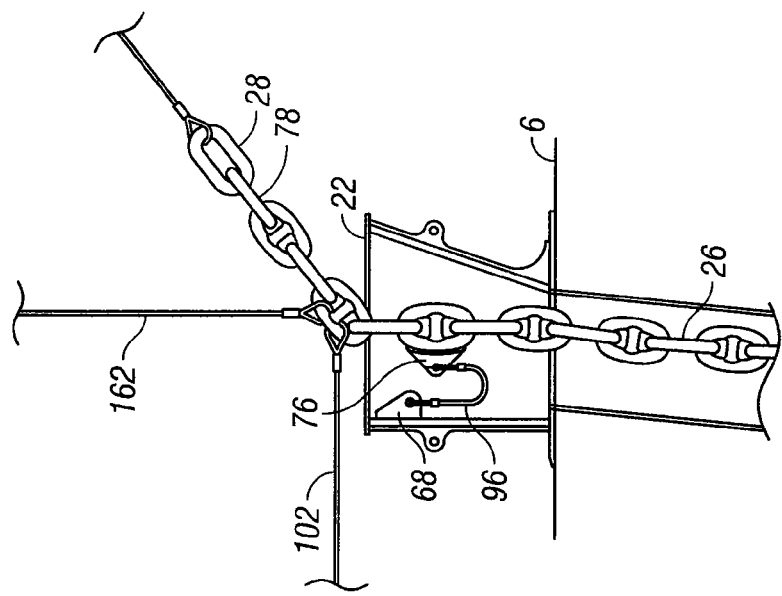
FIG. 30 is a schematic cross-sectional view, illustrating suspending the tail chain to provide slack for the sling supporting the tail chain and removal thereof.
Figure 29:
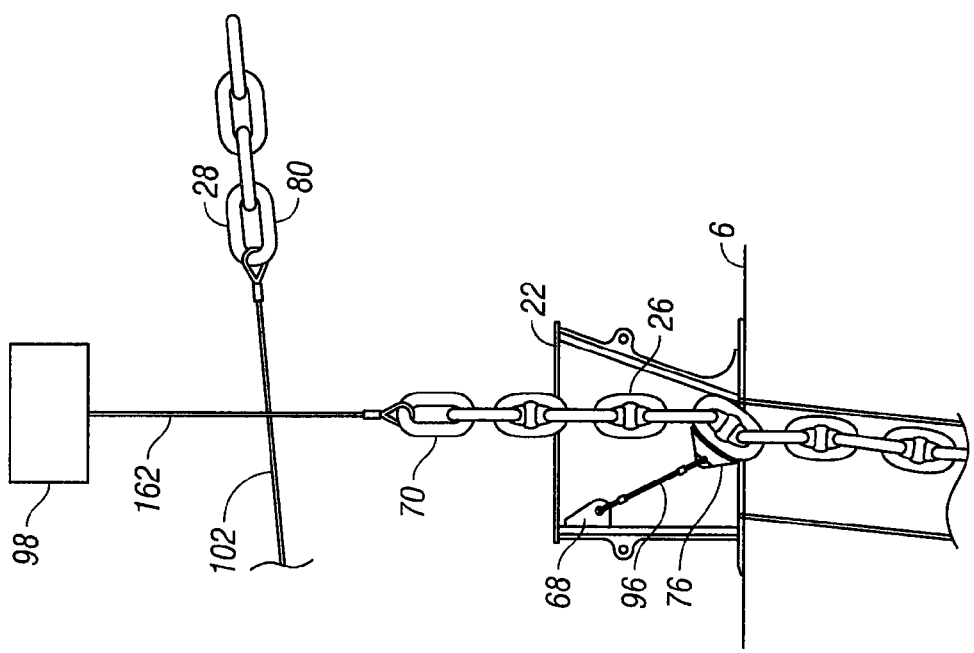
FIG. 29 is a schematic side cross-sectional view, illustrating pulling the platform chain and associated tail chain in proximity to each other for recoupling the tail chain with the platform chain.

Referring to FIGS. 29 and 30, each platform chain 28 can be recoupled with its respective tail chain 26 in the following manner. A hoist wire 162 from a chain hoist 98 can be coupled to an end link 70 of the tail chain 26 to pull the tail chain, while an air tugger wire 102 from an air tugger (not shown) can be coupled to an end link 80 of the platform chain 28 to pull the platform chain. The two end links 70, 80 can be pulled in close proximity and be recoupled together using a pear link 78 or other suitable coupler.

The air tugger wire 102 and hoist wire 162 can be disconnected from the end links and connected to the tail chain 26 just above the link with the chain padeye 76. The tugger and hoist take the load off of the sling 96 and the sling is disconnected from the padeye 68 on the chain guide 22. The tugger and hoist wires are slacked and disconnected. After both mooring lines 12A, 12B are recoupled to their respective tail chains, both mooring lines are hauled in to operating parameters.

The other pairs of mooring lines can be similarly adjusted and other wires repaired following similar or same principles.

Other procedures and variations are included in the disclosure, including for example, using alternative vessels and equipment, and different sequences. Further, while the disclosure describes the method and system in terms of a chain, the concepts and principles can be applied to other types of lines, including cables, and are within the scope of the disclosure and claims. Similarly, while the disclosure describes the floating platform in terms of a Spar, other floating platforms and vessels can be similarly moored, and thus the disclosure also applies to such structures.

Other and further embodiments utilizing one or more aspects of the inventions described above can be devised without departing from the spirit of Applicant's invention. Further, the various methods and embodiments of the catamaran system can be included in combination with each other to produce variations of the disclosed methods and embodiments. Discussion of singular elements can include plural elements and vice-versa. References to at least one item followed by a reference to the item may include one or more items. Also, various aspects of the embodiments could be used in conjunction with each other to accomplish the understood goals of the disclosure. Unless the context requires otherwise, the word "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. The term "coupled," "coupling," "coupler," and like terms are used broadly herein and may include any method or device for securing, binding, bonding, fastening, attaching, joining, inserting therein, forming thereon or therein, communicating, or otherwise associating, for example, mechanically, magnetically, electrically, chemically, operably, directly or indirectly with intermediate elements, one or more pieces of members together and may further include without limitation integrally forming one functional member with another in a unity fashion. The coupling may occur in any direction, including rotationally.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

What is claimed is:

1. A method for sharing of mooring lines, comprising:
   providing a first mooring line and a first tightening element for the first mooring line on a floating platform, the first mooring line being deployed from the platform to the seabed or another connecting structure, one end of the first mooring line being connected to the platform;
   providing a second mooring line and a second tightening element for the second mooring line on a floating platform, the second mooring line being deployed from the platform to the seabed or another connecting structure, one end of the second mooring line being connected to the platform;
   and, while the first mooring line is deployed from the platform to the seabed or another connecting structure and while the second mooring line being deployed from the platform to the seabed or another connecting structure:
      disconnecting a first portion of the first mooring line from a remainder of the first mooring line that is coupled to the platform to create an end of the first mooring line not connected to the floating platform, the first portion of the first mooring line being inboard relative to the first tightening element;
      disconnecting a first portion of the second mooring line from a remainder of the second mooring line that is coupled to the platform to create an end of the second mooring line not connected to the floating platform the first portion of the second mooring line being inboard relative to the second tightening element;
      coupling the first portion of the first mooring line with the first portion of the second mooring line to create a single shared line from the two lines with the ends of the shared line deployed to the seabed or other connecting structure;
      tightening the first mooring line through the tightening element to provide payout of line for the second mooring line; and
      loosening the second mooring line.

2. The method of claim 1, further comprising repairing the second mooring line when loosened with the payout of line from the first mooring line.

3. The method of claim 2, further comprising: tightening the second mooring line to provide payout of line for the first mooring line; and loosening the first mooring line.

4. The method of claim 3, repairing the first mooring line when loosened with the payout of line from the second mooring line.

5. The method of claim 4, further comprising: tightening the first mooring line; loosening the second mooring line; and decoupling the first mooring line from the second mooring line.

6. The method of claim 1, further comprising: tightening the second mooring line to provide payout of line for the first mooring line; and loosening the first mooring line.

7. The method of claim 1, wherein the coupling step includes coupling end-to-end at least the first mooring line and the second mooring line, the method comprising:
   paying out the first mooring line to access the first portion of the first mooring line coupled to the floating platform;
   paying out the second mooring line to access a first portion of the second mooring line coupled to the floating platform.

8. The method of claim 1, wherein disconnecting the first portion of the first mooring line from a remainder of the first mooring line comprises creating an end of the first portion of the first mooring line not connected to the floating platform;
   wherein disconnecting the first portion of the second mooring line from a remainder of the second mooring line includes creating an end of the first portion of the second mooring line not connected to the floating platform;
   and wherein coupling the first portion of the first mooring line with the first portion of the second mooring line includes coupling the end of the first portion of the first mooring line with the end of the first portion of the second mooring line not connected to the floating platform.

9. The method of claim 8, further comprising: repairing the loosened second mooring line; tightening the second mooring line; loosening the first mooring line; decoupling the first portion of the first mooring line from the first portion of the second mooring line; reconnecting the first portion of the first mooring line with the remainder of the first mooring line; and reconnecting the first portion of the second mooring line to the remainder of the second mooring line.

10. The method of claim 1, further comprising: lifting the loosened second mooring line from a subsea elevation; repairing the second mooring line; and lowering the second mooring line.

11. The method of claim 10, further comprising: disconnecting the second mooring line from the seabed or other connecting structure; lifting the disconnected second mooring line; repairing the disconnected second mooring line; reconnecting the second mooring line to the seabed or another connecting structure; and lowering the second mooring line.

12. The method of claim 11, further comprising: tightening the second mooring line to provide payout of line for the first mooring line; and loosening the first mooring line.

13. The method of claim 12 further comprising: lifting the loosened first mooring line from a subsea elevation; repairing the first mooring line; and lowering the first mooring line.

14. The method of claim 13, further comprising: disconnecting the first mooring line from the seabed or other connecting structure; lifting the disconnected first mooring line; repairing the disconnected first mooring line; reconnecting the first mooring line to the seabed or other connecting structure; and lowering the first mooring line.

15. The method of claim 14, further comprising: tightening the first mooring line; loosening the second mooring line; and decoupling the first mooring line from the second mooring line.

16. A system for sharing of mooring lines coupled on a floating platform, comprising:
a first mooring line;
a first tightening element for the first mooring line coupled on the floating platform, the first mooring line being deployed from the platform to the seabed or another connecting structure, one end of the first mooring line being connected to the platform;
a second mooring line;
a second tightening element for the second mooring line on the floating platform, the second mooring line being deployed from the platform to the seabed or another connecting structure, one end of the second mooring line being connected to the platform;
a coupling link configured to be decoupled from a first portion of the first mooring line and from a remainder of the first mooring line that is coupled to the platform to create an end of the first mooring line not connected to the floating platform, the first portion of the first mooring line being inboard relative to the first tightening element while the first mooring line is deployed from the platform to the seabed or another connecting structure;
a coupling link configured to be decoupled from a first portion of the second mooring line and from a remainder of the second mooring line that is coupled to the platform to create an end of the second mooring line not connected to the floating platform the first portion of the second mooring line being inboard relative to the second tightening element, while the second mooring line is deployed from the platform to the seabed or another connecting structure;
a coupling element separate from the tightening elements adapted to couple the ends of the first portions of the two separate mooring lines to create a single shared line from the two separate mooring lines; and
the first tightening element being adapted to tighten the first mooring line to provide payout of line for the second mooring line to allow loosening of the second mooring line.

17. The system of claim 16, further comprising at least one holding element coupled between the first and second tightening elements and adapted to guide the mooring lines between the first and second tightening elements.

* * * * *